United States Patent [19]

Kalina

[11] 4,001,090
[45] Jan. 4, 1977

[54] PROCESS AND APPARATUS FOR THE CULTURE OF MICROORGANISMS

[75] Inventor: Vladimir Kalina, Lausanne, Switzerland

[73] Assignee: Societe d'Assistance Technique Pour Produits Nestle S.A., Lausanne, Switzerland

[22] Filed: May 27, 1975

[21] Appl. No.: 580,744

[30] Foreign Application Priority Data

May 28, 1974 Switzerland ................... 7249/74

[52] U.S. Cl. ............................ 195/109; 195/142
[51] Int. Cl.$^2$ .................... C12B 1/14; C12B 1/16
[58] Field of Search ........................ 195/109, 142

[56] References Cited

UNITED STATES PATENTS

| | | | |
|---|---|---|---|
| 3,114,677 | 12/1963 | Stich | 195/142 |
| 3,630,848 | 12/1971 | Lefrancois | 195/109 |
| 3,642,577 | 2/1972 | Gorring | 195/109 |
| 3,793,152 | 2/1974 | Sassa | 195/142 |
| 3,847,748 | 11/1974 | Gibson et al. | 195/142 |

*Primary Examiner*—Alvin E. Tanenholtz
*Attorney, Agent, or Firm*—Watson Leavenworth Kelton & Taggart

[57] ABSTRACT

A process for the aerobic culture of a microorganism in a fluid nutrient medium therefor containing at least one source of carbon assimilable by the microorganism, in which a culture broth consisting of the fluid nutrient medium and of a cellular mass of the microorganism is circulated in a closed loop between an upper level and a lower level, in which the broth is subjected, in a fermentation zone extending along an ascending side of the loop from the lower level, to the combined action of the frictional forces of bubbles of an oxygen containing gas or of oxygen released under pressure into the broth, a mechanical force applying an upward thrust and at least one couple of mechanical forces acting in a horizontal plane.

13 Claims, 1 Drawing Figure

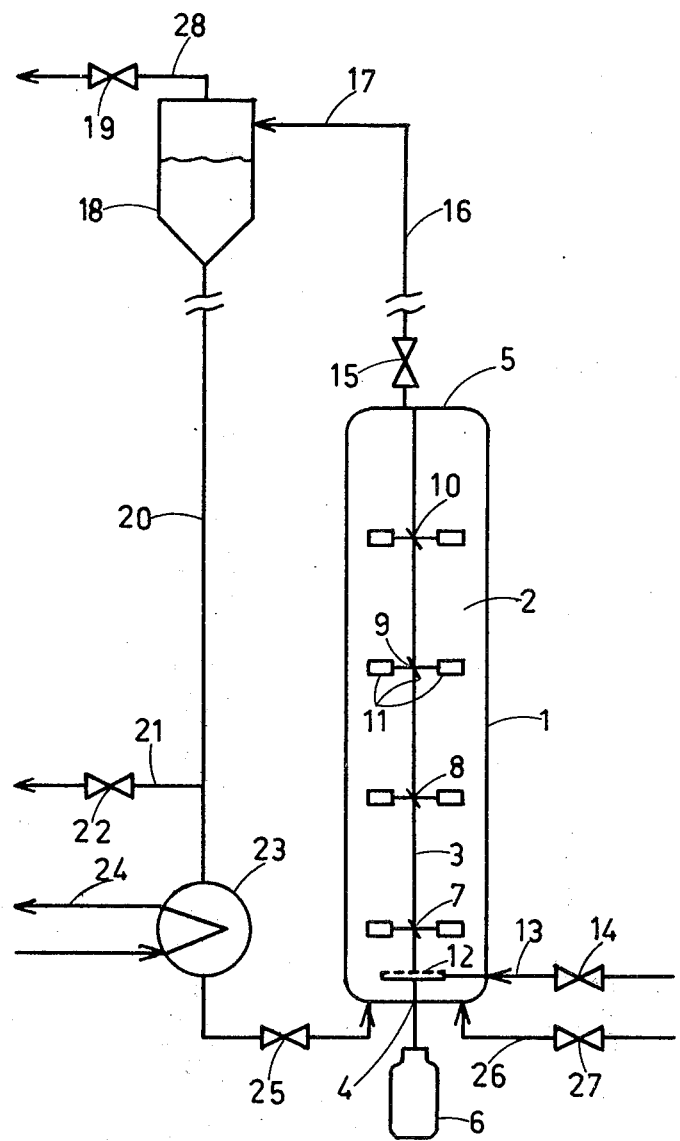

PROCESS AND APPARATUS FOR THE CULTURE OF MICROORGANISMS

This invention is concerned with the field of industrial fermentation for the production of proteins on a large scale, and relates to a process for the aerobic culture of a microorganism in a fluid nutrient medium containing at least one source of carbon assimilable by the microorganism, in which a culture broth consisting of the fluid nutrient medium and of a cellular mass of the microorganism is made to circulate in a closed loop between a higher level and a lower level.

The high-yield culture of aerobic microorganisms, more especially on petroleum fractions or on substrates derived from petroleum which contain only a very little oxygen, requires extremely high oxygen transfer rates which cannot effectively be reached on an industrial scale in conventional stirred tank fermenters or circulation tower fermenters. In the present context, a high-yield culture is a culture by which it is possible to produce from 10 to 20 g of bacteria or yeasts per liter of culture broth per hour which, in the case of substrates corresponding to the formula $C_nH_{2n+2}$ or $C_nH_{2n+1}$ OH for example, requires oxygen transfer rates well in excess of 500 mMols of $O_2$ per liter per hour. High oxygen transfer rates necessitate high carbon dioxide transfer rates. Now the extent of these two transfers should not cause any inhibiting effects attributable to excessive partial oxygen and carbon dioxide pressures in the gas brought into contact with or circulating in the culture broth.

Although it is possible to increase the oxygen transfer rate in an ordinary stirred tank fermenter by using oxygen-enriched air, an increase in the removal rate of the carbon dioxide produced during fermentation can only be obtained by considerably increasing aeration. However, it is not possible indefinitely to increase the throughput of air in a conventional stirred tank fermenter without before very long exceeding a limit beyond which the foam formed can no longer be controlled. In this respect, the situation is more favourable in the case of a circulation tower fermenter equipped with an effective separation system connected to the top of the tower, whilst the at least partly degassed fluid is recycled through the bottom of the tower. However, if it is desired in this case to increase aeration to obtain the oxygen transfer rate required for a high-yield culture, a limit is again encountered, appearing with the formation of preferential paths followed by the gas bubbles in an inadequately agitated broth. Accordingly, the increase in the relative rate of flow of the gas in relation to the culture broth is not reflected in the required effect of an improvement in the oxygen transfer rate, but instead in an inhibiting effect attributable to the gradients thus established, resulting ultimately in a pure loss of energy. Although it is possible to improve the situation by arranging obstacles, such as screens, in the path followed by the ascending gas, this can only be done if the obstacles in question do not in turn cause the development of excessive oxygen partial pressure gradients which create an inhibiting pressure zone in the lower part of the tower.

The high-yield culture of microorganisms on low-oxygen substrates also involves serious heat-transfer problems. For example, in a process where the heat of fermentation exceeds 8000 kcal per kg of cells produced at a production rate of 15 g per liter per hour, the increase in temperature of the medium amounts to 2° C per minute if the medium is not cooled. Accordingly, it is essential to provide an effective cooling system. A cooling system involving heat exchange inside the fermentation zone would not be recommended in the case of a high-yield culture in view of the undesirable obstacles which the cooling surfaces required to maintain a fermentation temperature of the order of 30° to 40° C would constitute. For this reason, the cooling system should be provided outside the fermentation zone. Unfortunately, the maintenance of low temperature gradients by means of a system of this kind requires a high speed of circulation of the fluid. However, it is only possible to obtain a high rate of circulation in a conventional circulation tower fermenter at the expense of a reduction in the oxygen transfer rate which goes against the required objective of a maximum growth rate.

The present invention provides a process for the aerobic culture of a microorganism in a fluid nutrient medium therefor containing at least one source of carbon assimilable by the microorganism, in which a culture broth consisting of the fluid nutrient medium and of a cellular mass of the microorganism is circulated in a closed loop between an upper level and a lower level, in which the broth is subjected, in a fermentation zone extending along an ascending side of the loop from the lower level, to the combined action of the frictional forces of bubbles of an oxygen containing gas or of oxygen released under pressure into the broth, a mechanical force applying an upward thrust and at least one couple of mechanical forces acting in a horizontal plane. The broth is preferably cooled outside the fermentation zone.

Culturing is with advantage carried out continuously and it is possible, along a descending side of the circuit connected to the ascending side at the higher and lower levels, at least partly to degas the broth, to cool it and to recover at least a fraction of the cellular mass present in it whilst, at the same time, enriching the broth recycled into the fermentation zone with nutrient substances.

The advantages afforded by the process according to the invention include the uniform dispersion of the gas in the fluid for a high aeration rate, the homogeneity of the culture broth along the fermentation zone without the appearance of inhibiting gradients, the maximum extension of the fermentation zone into the space available for this purpose and the effectiveness of heat transfer for a high rate of circulation of the fluid. It is also possible by virtue of the process according to the invention to reduce the total amount of energy used for the transfer of a given quantity of oxygen per unit volume of the aerated fluid in relation to the quantity used in a conventional process. Finally, another advantage of the process according to the invention is its flexibility which enables it to be adapted to the characteristics of a wide variety of cultures both in regard to the growth rate of the microorganisms and in regard to the amount of heat given off during fermentation or in regard to the level of oxygen or carbon dioxide partial pressures to be observed.

It is advisable to maintain at the top of a fermentation zone terminating below the upper level a pressure higher than that prevailing at the upper level. It is possible in this way to consolidate the advantages of the process both in regard to its flexibility and in regard to the extent of oxygen transfer by virtue of the fact that that part of the circuit between the top of the fermentation zone and the upper level may be used for expanding the gases injected and liberated under pressure, whilst the drop in pressure from the bottom to the top of the fermentation zone may ideally be limited to substantially that occasioned by the reducing height of the column of broth.

The present invention also relates to an apparatus for carrying out the process, consisting of a closed loop with an ascending side and a descending side communicating with one another at an upper level and at a lower level, in which the ascending side comprises a chamber forming a fermentation zone rising from the lower level and comprising means for injecting gas at its lower end, means for mechanically propelling a culture broth and means for mechanically mixing the broth.

It is of advantage to incorporate in the descending side means for degassing the broth and means for cooling the broth. As any expert will have appreciated from the foregoing, the apparatus according to the invention, by its very design, is particularly intended for the continuous treatment of large quantities of broth. Thus, the volume of the fermentation chamber may be more than 50 cubic meters and even more than 100 cubic meters, whilst for a residence time of the broth in the chamber of the order of one minute, throughput may amount to between 50 and 100 cubic meters per minute. In order, under these conditions, to limit the dimensions of the cooling system and the quantities of cooling fluid required, it is advisable to provide a heat exchanger arranged between a compressor and a condenser for the cooling fluid, namely an evaporation exchanger. With exchangers of this kind, which may function with throughputs of from 10 to 20 tonnes per hour of a cooling fluid, such as a freon, it is possible to reduce the size of the exchanger surfaces and hence to reduce the pressure losses whilst at the same time profiting from the temperature difference which is favourable to the transfer of heat. With regard to the degassing means, namely the means for removing nitrogen of the air (in cases where air is injected into the fermentation chamber) the carbon dioxide given off during fermentation, and the oxygen which has not been used, it is possible to incorporate at the top of the descending side a surface-effect separator or a hydrocyclone.

Means for recovering cellular material carried by the broth may be connected to the descending side, whilst a feed pipe for nutrient substances may be connected to the lower part of the fermentation chamber. The recovery means may consist of a branch pipe through which part of the degassed broth may be delivered to means for separating the cellular mass from the broth, the broth thus freed from its cellular mass being returnable through a recycling pipe to the descending side or into the fermentation chamber. In this respect, it is reasonable to consider that, during working of the process according to the invention, the quantity of broth treated per hour to separate the cellular mass from it may be of the order of the quantity per minute of broth entering the fermentation chamber. The nutrient substances to be injected through the feed pipe into the fermentation chamber for correspondingly replenishing the substances consumed by a suitable microorganism cultivated in the chamber may be, for example, a hydrocarbon, an alcohol or a sugar as carbon source and ammonia or urea as nitrogen source.

The means for mechanically propelling the broth into the fermentation chamber may consist of at least one impeller rotating in a horizontal plane and capable of thrusting the broth upwards, thus reinforcing the ascending effect of the friction of the bubbles or air or oxygen released under pressure at the bottom of the chamber. The means for mechanically mixing the broth in the chamber may consist of a number of sets of rotary blades or paddles arranged at intervals from one another and one above the other. These sets may be mounted on a common vertical rotary shaft driven by a motor. Since a secondary effect of the broth-mixing action of these sets of blades is to create turbulent currents which offer a certain resistance to the ascent of the broth in the chamber, it may be advisable to provide the blades or paddles, or at least some of them, with an inclination relative to the horizontal plane or with such a configuration that at least one of the sets is in the form of an impeller and is capable of applying an upward thrust to the broth. It is clear that any combination of the propelling and mixing means is possible.

The fermentation chamber need not necessarily extend over the entire height comprised between the upper level and the lower level; it may instead be confined to a restricted passage opening into a pipe which terminates at the upper level where it opens into the top of the descending side. It is thus possible to maintain at any level of the chamber, whose height may be of the order of eight to ten metres, a pressure substantially equal to the pressure under which air or oxygen is injected into the bottom of the chamber less the hydrostatic pressure of the column of aerated broth situated between the bottom of the chamber and the level in question. Thus, if, in order to obtain in the fermentation chamber a fairly high oxygen transfer rate, i.e. well in excess of 500 mMols of $O_2$ and even higher than 900 mMols of $O_2$ per liter per hour, it may be necessary to have a pressure of at least 3 to 3.5 atmospheres absolute in a broth containing, in dispersion, a quantity of air of approximately 40% by volume, then the excess energy of the feed gas at the output end of the chamber may be utilised by making the pipe leading from the constricted passage to the upper level, where a pressure aound atmospheric may prevail, function as an air pump.

The advantage of this separation between the transfer of oxygen and the expansion of the feed gas is that it is possible completely to eliminate pressure losses, especially the pressure loss attributable to the cooling system, and to obtain circulation of the broth through the apparatus whilst, at the same time, maintaining throughout the fermentation zone a pressure sufficiently high and uniform to obtain the required oxygen transfer rates. It is possible to provide a restricted passage in the form of a constriction, diaphragm or succession of screens partly overlapping one another along a passage leading from the top of the chamber to the pipe which leads to the upper level.

One embodiment of the apparatus used for carrying out the process according to the invention is described by way of example in the following with reference to the accompanying drawing which is a diagrammatic vertical section through this exemplary embodiment.

A vertically elongated metal chamber 1 forms a fermentation zone 2. A rotating shaft 3 extends upwards throughout the entire fermentation zone, in other words from the lower level 4 of the apparatus to the top 5 of the chamber. The shaft 3 is driven by an electric motor 6 arranged below the chamber. Sets of blades or paddles 7, 8, 9 and 10 are mounted at regular intervals on the shaft 3. Each set, for example the set 8, consists of four flat paddles 11. The plane of each paddle is inclined in the same direction relative to the vertical plane defined by its free end and the shaft 3 so that each set may be used both for mixing the culture broth in the process of fermentation in the zone 2 and for propelling the broth upwards. The gas-injecting means 12 mounted at the bottom of the chamber consists of a set of horizontal pipes drilled with small holes. A feed pipe 13 for gas, whose rate of flow is controlled by a gas feed valve 14, is intended to supply the pipes 12 with the gas which has to be released under the required pressure into the bottom of the chamber 1. A back-pressure valve 15 arranged in the top of the chamber 1 connects the upper end of the fermentation zone 2 to an expansion pipe 16 which leads to the upper level 17 of the apparatus. This valve 15 defines a restricted passage for the aerated broth and, hence, has to prevent any loss of pressure which is not due to a reduction in the height of the column of aerated broth in the chamber. The expansion pipe 16 thus forms the upper part of the ascending side of the apparatus. Its height is such that it simultaneously enables the pressure losses in the descending side to be compensated, the resistances which have not been completely compensated in the fermentation chamber by the propulsive effect of the two sets of blades in impeller form to be overcome and the required rate of circulation of the broth in the closed loop, formed by the ascending side and the descending side of the apparatus communicating with one another at the upper and lower levels 17 and 4, respectively, to be maintained. A gas separation means 18, in the present case a cyclone, is the first component of the descending side. An exit pipe 28 for the gas which is either not liberated or not consumed during fermentation is connected to the upper part of the cyclone 18 and opens into the atmosphere through an outlet valve 19 intended to control the pressure gradients in the apparatus. The lower part of the cyclone 18, intended to receive the broth at least partly separated from the gases, is connected to a return pipe 20. In the pipe 20, the broth has a relatively high density, guaranteeing the operation as an air pump of the pipe 16 in which the aerated and fermented broth circulates in the form of a dispersion delivered under pressure through the back-pressure valve 15. A pipe for recovering cellular material carried by the at least partly degassed broth, or branch pipe 21, is connected to the return pipe 20. The throughput of broth to be treated to separate the cellular material therefrom is controlled by a recovery valve 22 connected in series to the pipe 21. The pipe 21 leads to a means for recovering cellular material, for example a centrifuge (not shown). A cooling means 23, in the present case an evaporation-type heat exchanger, is connected in series to the return pipe 20 for circulation of the broth, and in series between a compressor and a condenser (not shown) for circulation of the cooling fluid 24. A final section of the return pipe 20 leads from the exchanger 23 to the bottom of the fermentation chamber 1 via a valve 25 for controlling the rate of circulation of the broth in the apparatus. Finally, the reference 26 denotes a feed pipe for nutrient substances connected to the lower part of the fermentation chamber. The pipe 26 passes through a valve 27 for controlling the rate of flow of a nutrient fluid delivered by a mixer (not shown). A pipe for recycling the broth removed via the pipe 21 and then separated from its cellular material may be connected to this mixer for nutrient substances. Thus, what may be called the secondary closed loop, in which circulates that part of the broth from which the cellular material may be continuously removed, joins up with the closed loop in which all or almost all the both circulates.

The process and apparatus of the present invention are particularly useful for the culture of microorganisms for the production of intracellular and extracellular substances, such as proteins and amino acids.

We claim:

1. A process for the aerobic culture of a microorganism in a fluid nutrient medium therefor containing at least one source of carbon assimilable by the microorganism, comprising circulating a culture broth consisting of the fluid nutrient medium and a cellular mass of the microorganism in a closed loop flow course having ascending and descending sides extending between upper and lower levels of said closed loop, there being a fermentation zone extending upwardly along the ascending side of the loop from said loop lower level and having a top terminating below said loop upper level, subjecting said culture broth while flowing through said fermentation zone to the combined action of the frictional forces of bubbles of an oxygen containing gas or of oxygen released under pressure into the broth, a mechanical force applying an upward thrust to the culture broth, and at least one couple of mechanical forces acting on the broth in a horizontal plane, and imposing a back pressure on the culture broth at the top of the fermentation zone whereby the pressure prevailing at the top of the fermentation zone is maintained at a higher value than the pressure prevailing at the said upper level of said loop.

2. A process as claimed in calim 1, in which the broth is subjected to a cooling operation outside the fermentation zone to remove heat therefrom.

3. A process as claimed in claim 2, in which the broth while flowing in the descending side of said loop is at least partly degassed, subjected to said cooling operation and at least part of the cellular mass present therein is recovered therefrom.

4. A process as claimed in claim 3, in which after recovery of the cellular mass the broth is enriched by introducing nutrient substances thereto, said enriched broth being recycled to the fermentation zone.

5. Apparatus for the aerobic culture of microorganisms, comprising means defining a closed loop flow course wherein a culture broth can be circulated, said closed loop having ascending and descending sides thereof and communicating with each other at respective upper and lower loop levels, means defining a fermentation chamber in the ascending side of said loop, said fermentation chamber extending upwardly a distance from said loop lower level and having a top disposed a distance below said loop upper level, means for injecting gas under pressure into said fermentation chamber at the lower end thereof, means for mechanically propelling culture broth upwardly from the lower end of said fermentation chamber, means for applying at least one couple of mechanical forces acting in a horizontal plane on broth in said fermentation chamber, and means for imposing a back pressure on the culture broth at the top of said fermentation chamber whereby the pressure at the top of said fermentation chamber is maintained at a higher value than the pressure prevailing at the upper level of said loop.

6. An apparatus as claimed in claim 5 further comprising means for degassing the broth, and means for cooling the broth, said two last-mentioned means being disposed in the descending side of said loop.

7. An apparatus as claimed in claim 6, in which the cooling means is a heat exchanger arranged between a compressor and a condenser for the cooling fluid.

8. An apparatus as claimed in claim 5 further comprising means for recovering cellular material disposed in the descending side of said loop, and a feed pipe connected to the lower part of the fermentation zone for adding nutrient substances to the culture broth.

9. An apparatus as claimed in claim 5 in which the mechanical propulsion means comprises at least one rotary impellar.

10. An apparatus as claimed in claim 5 in which the mechanical mixing means comprises one or more sets of rotatable blade means mounted on a shaft at vertical intervals from one another.

11. An apparatus as claimed in claim 10, in which at least one of the sets of mixing blade means is arranged as an impeller.

12. An apparatus as claimed in claim 5 in which a restricted passage embodying a back-pressure valve is provided at the top of the fermentation zone.

13. An apparatus as claimed in claim 12, in which the restricted passage is below the upper level of said loop.

* * * * *